(12) United States Patent
Phillips

(10) Patent No.: US 8,052,697 B2
(45) Date of Patent: Nov. 8, 2011

(54) CLAMP DEVICE TO PLICATE THE STOMACH

(76) Inventor: Edward H. Phillips, Beverly Hills, CA (US)

( * ) Notice: Subject to any disclaimer, the term of this patent is extended or adjusted under 35 U.S.C. 154(b) by 589 days.

(21) Appl. No.: 11/996,495

(22) PCT Filed: Jul. 21, 2006

(86) PCT No.: PCT/US2006/028288
§ 371 (c)(1),
(2), (4) Date: Jun. 16, 2008

(87) PCT Pub. No.: WO2007/013995
PCT Pub. Date: Feb. 1, 2007

(65) Prior Publication Data
US 2008/0269788 A1 Oct. 30, 2008

(51) Int. Cl.
*A61B 17/08* (2006.01)
(52) U.S. Cl. .......... 606/151; 606/157; 606/192; 600/31; 600/37
(58) Field of Classification Search .......... 606/151–158, 606/190–199, 201, 202; 623/23.65, 23.68; 600/29–32, 37, 207; 128/899, 99.1–110.1
See application file for complete search history.

(56) References Cited

U.S. PATENT DOCUMENTS

| | | | | |
|---|---|---|---|---|
| 4,558,699 A | * | 12/1985 | Bashour | 606/157 |
| 4,586,501 A | * | 5/1986 | Claracq | 606/158 |
| 5,601,604 A | * | 2/1997 | Vincent | 606/216 |
| 7,288,100 B2 | * | 10/2007 | Molina Trigueros | 606/151 |
| 7,662,087 B2 | * | 2/2010 | Bailly et al. | 600/37 |
| 7,691,053 B2 | * | 4/2010 | Viola | 600/37 |
| 7,871,416 B2 | * | 1/2011 | Phillips | 606/151 |

* cited by examiner

*Primary Examiner* — Tuan Nguyen
(74) *Attorney, Agent, or Firm* — Frederick Gotha

(57) ABSTRACT

A medical device for clamping the stomach in morbid obesity surgery consists of a silicone frame that is essentially U-shaped, having opposing legs self-hinged to a bight portion interconnecting the legs. The opposing legs have sufficient stiffness to permit limited bending and have inner surfaces that sealingly carry an inflatable balloon which can be selectively inflated or aspirated after the device has been clamped to the stomach to adjust the gastric restriction stoma. A flexible latch member carried by one of the legs has at least one serration which is inserted into a latch cavity of the opposing leg to lock the opposing legs in fixed spaced relationship. Lumens within the legs communicate with a fluid supply source and respective inflatable balloon for selective inflation or aspiration of the inflatable balloons. The medical device for clamping the stomach may be self-adjusting upon distention and contraction of the proximal stomach. A platform member having finger extensions which are biased to remain in compressive engagement with the anterior surface of the proximal stomach reduce the gastric restriction stoma from its nominal position upon distention of the proximal stomach and enlarge the reduction upon contraction of the proximal stomach to the nominal position.

6 Claims, 17 Drawing Sheets

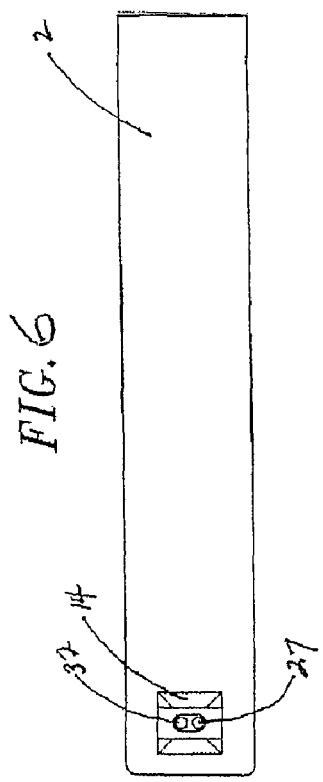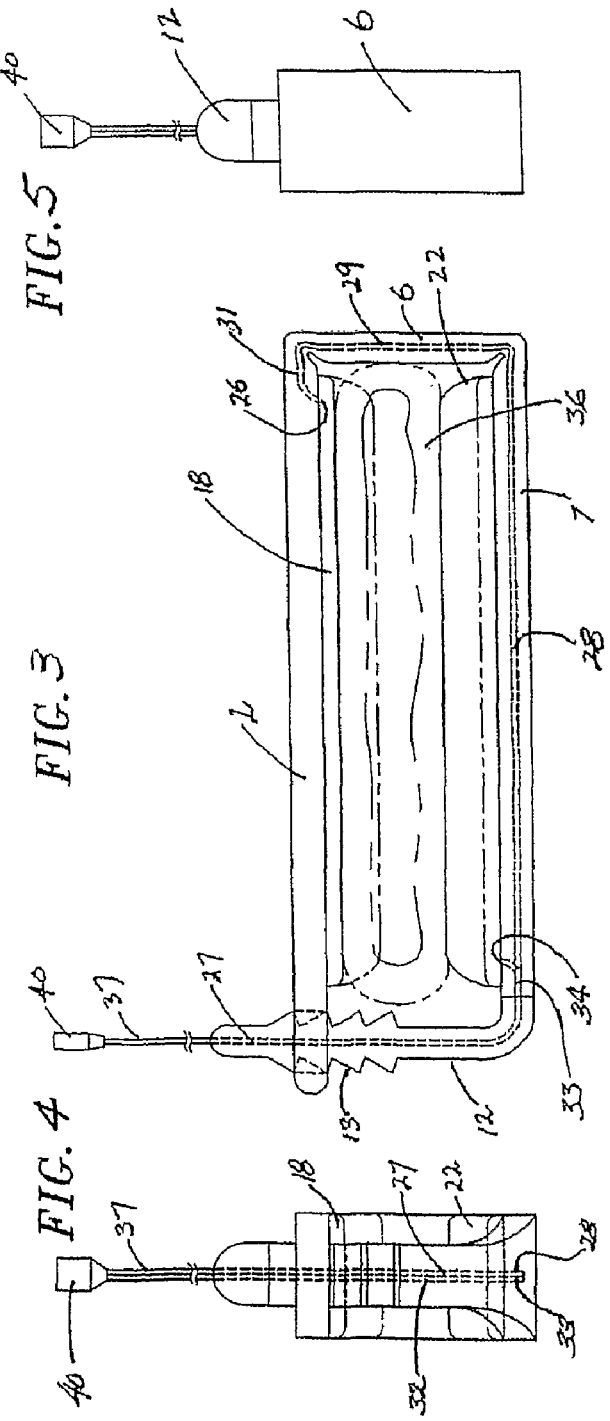

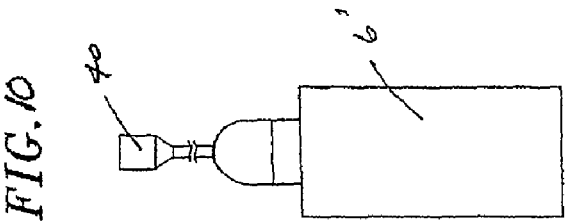
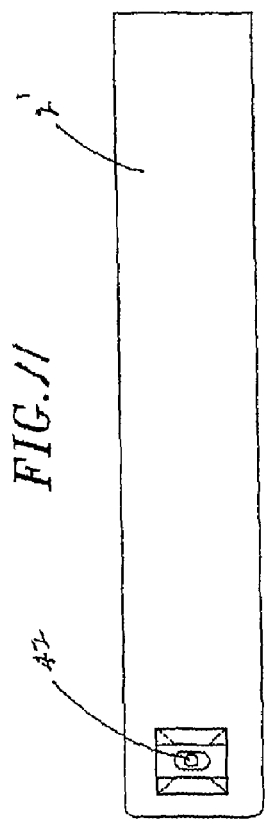
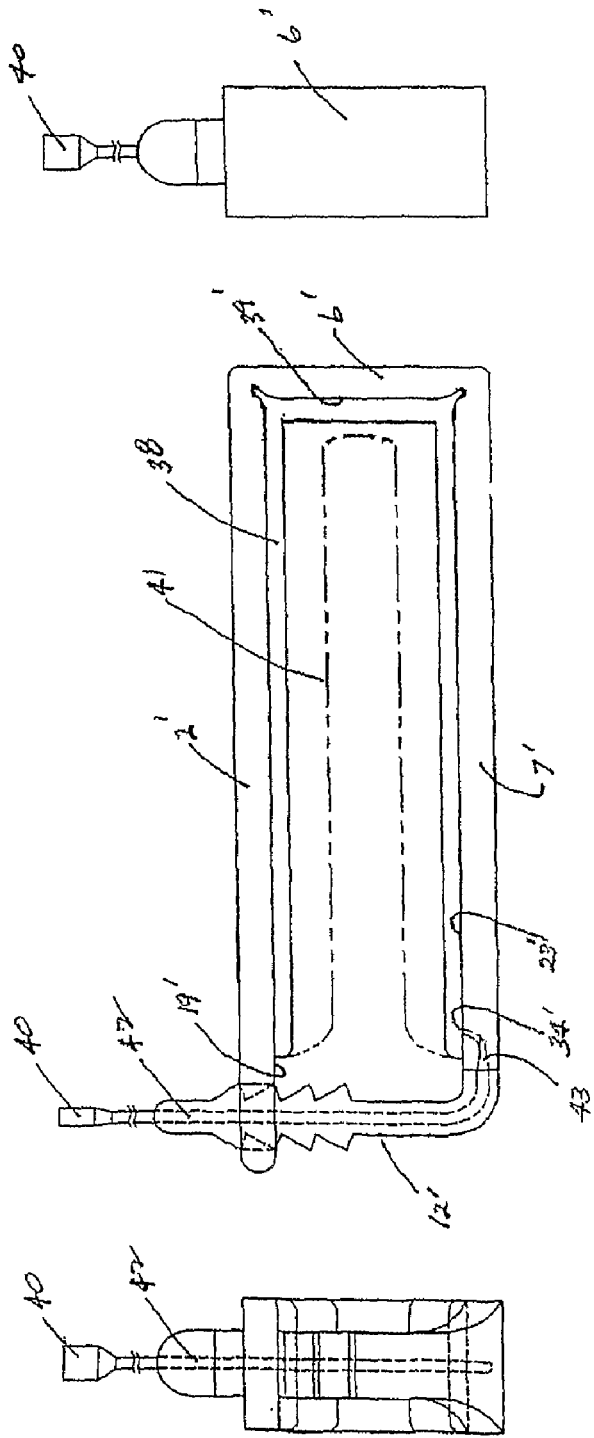

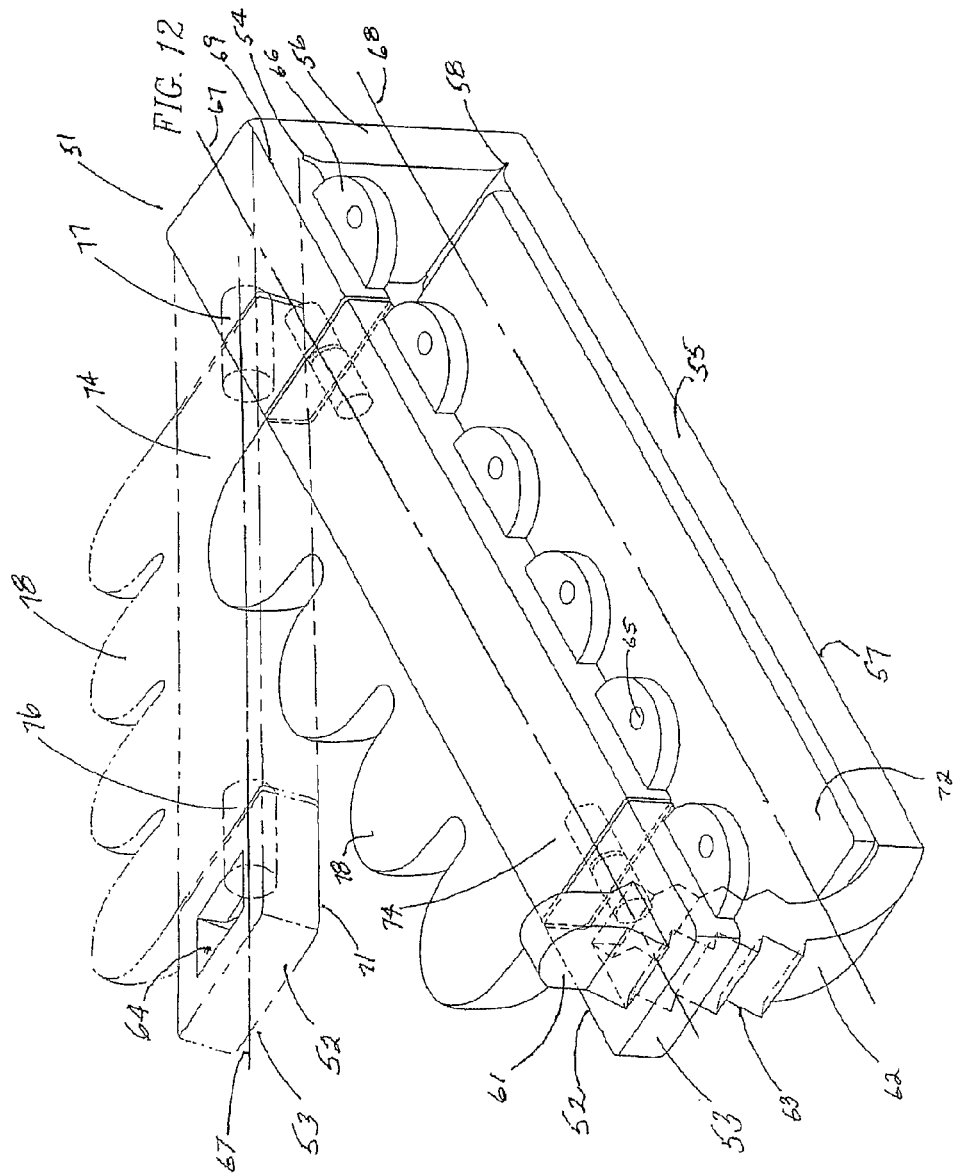

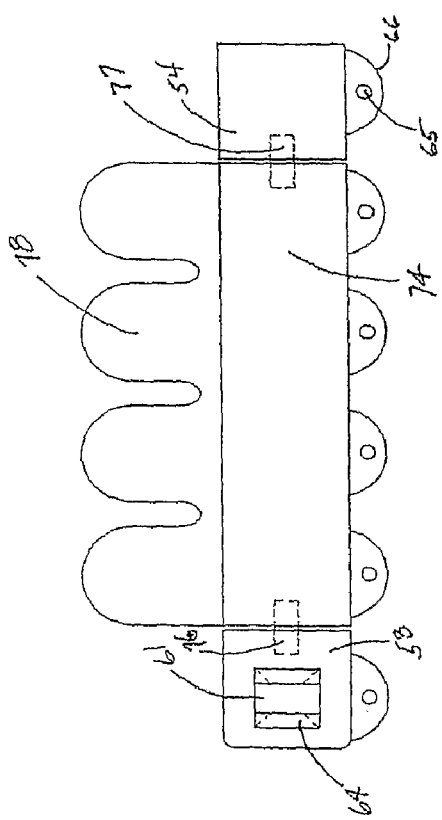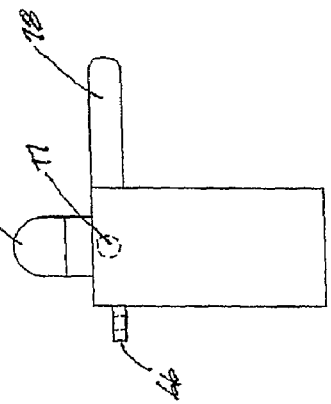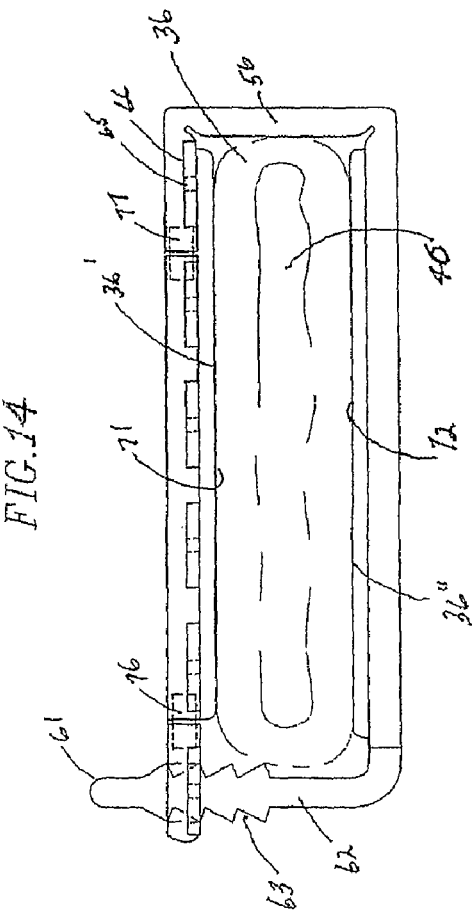

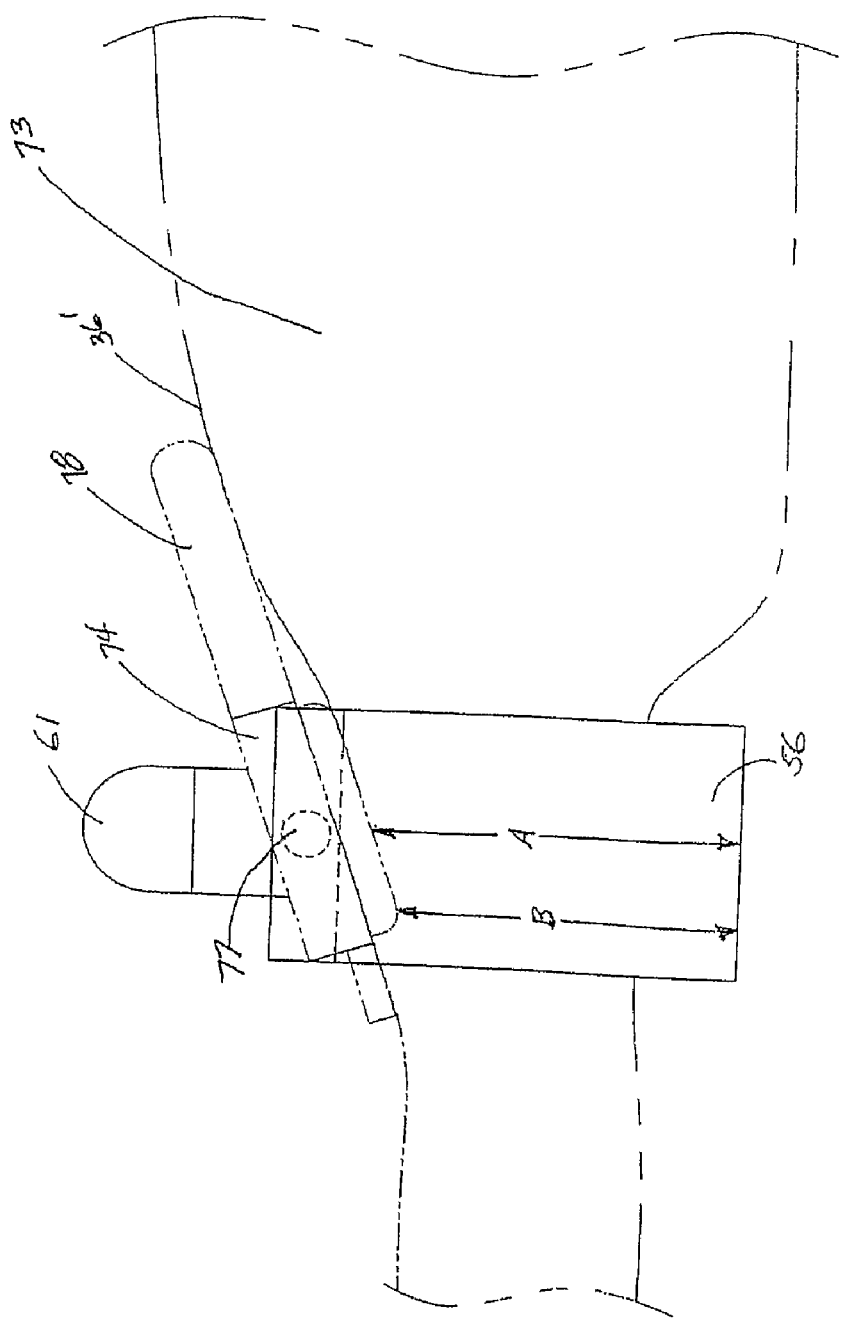

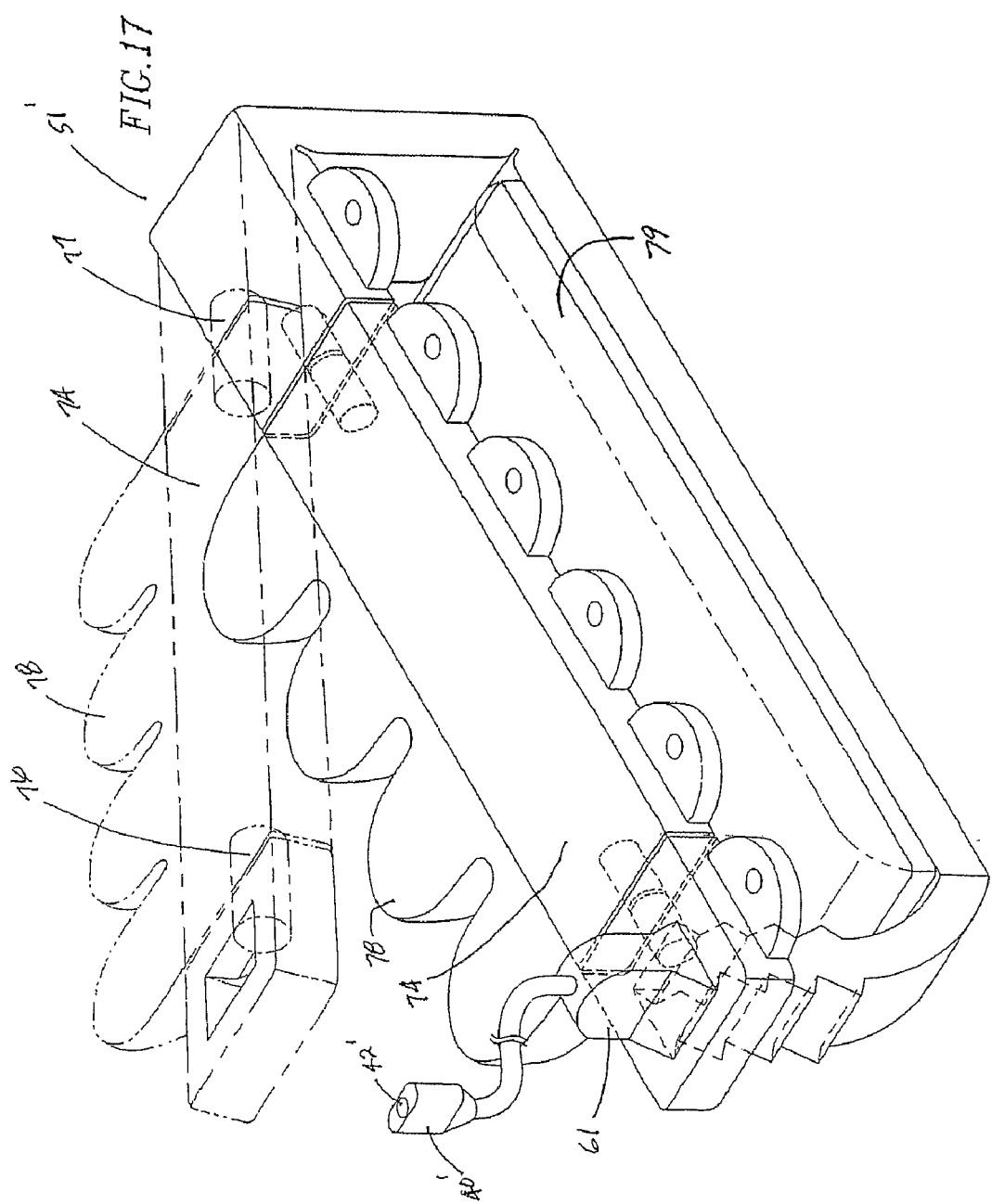

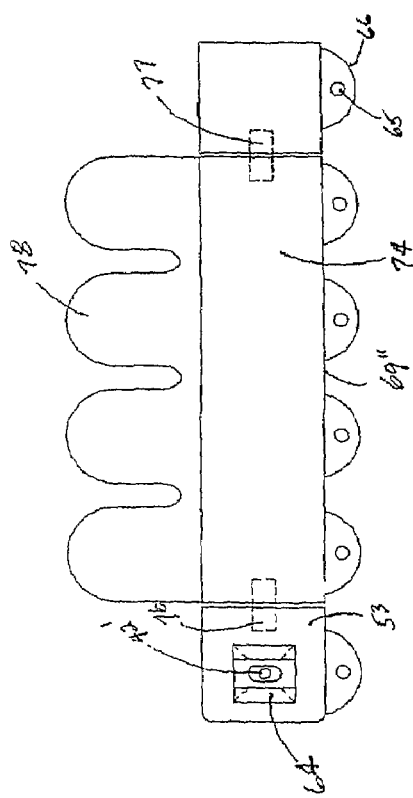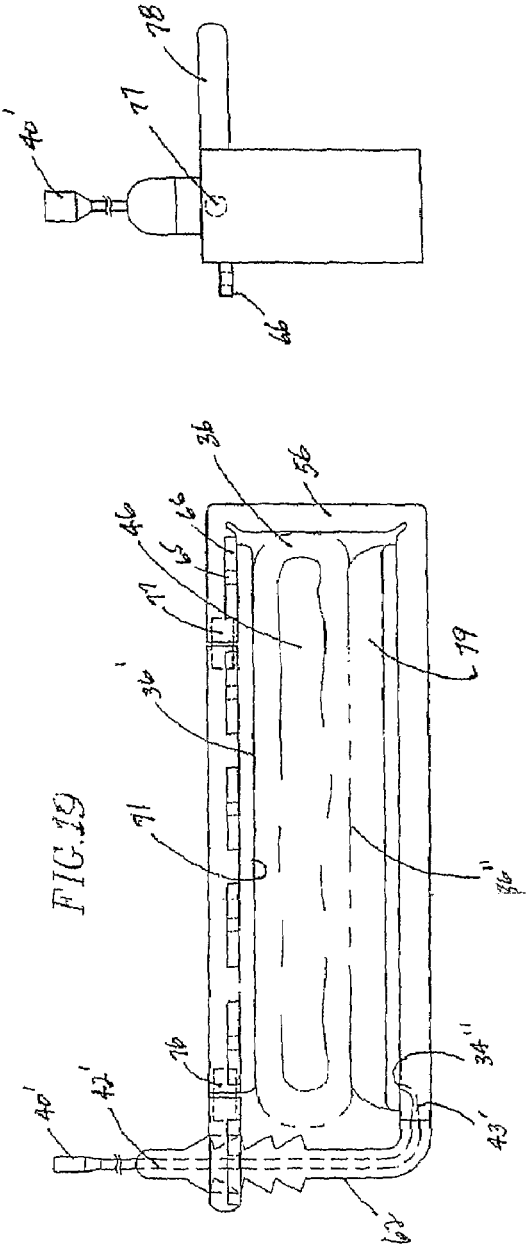

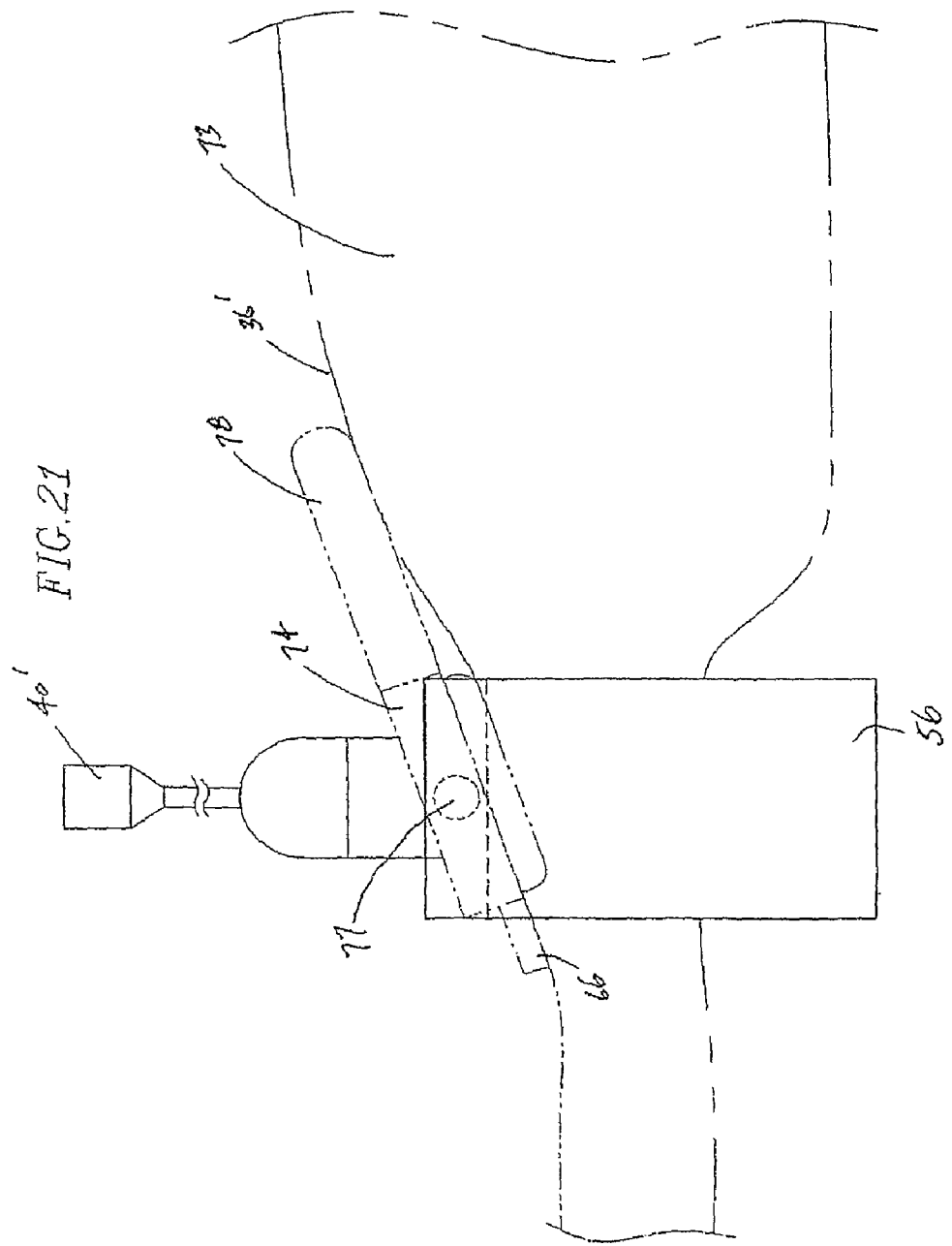

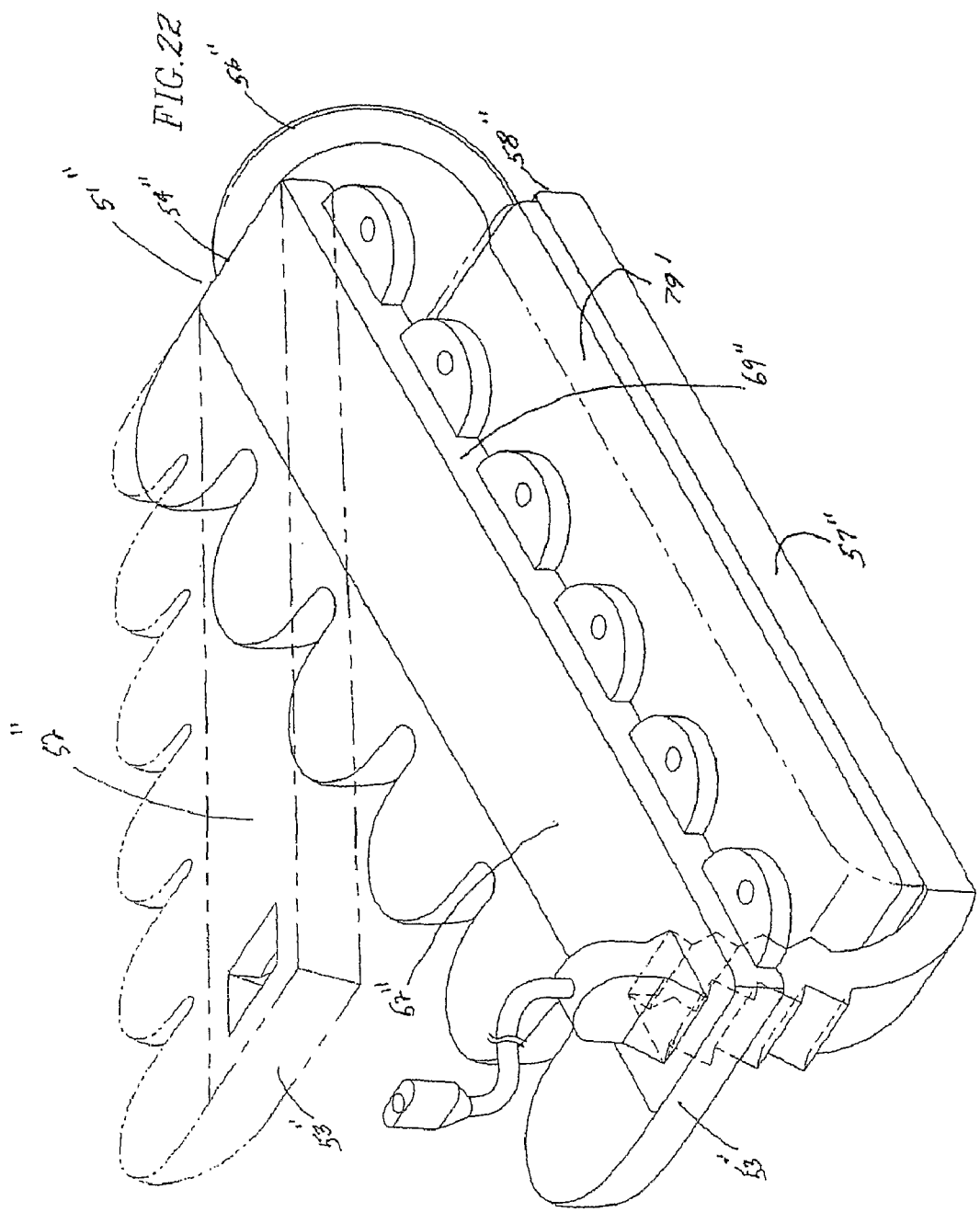

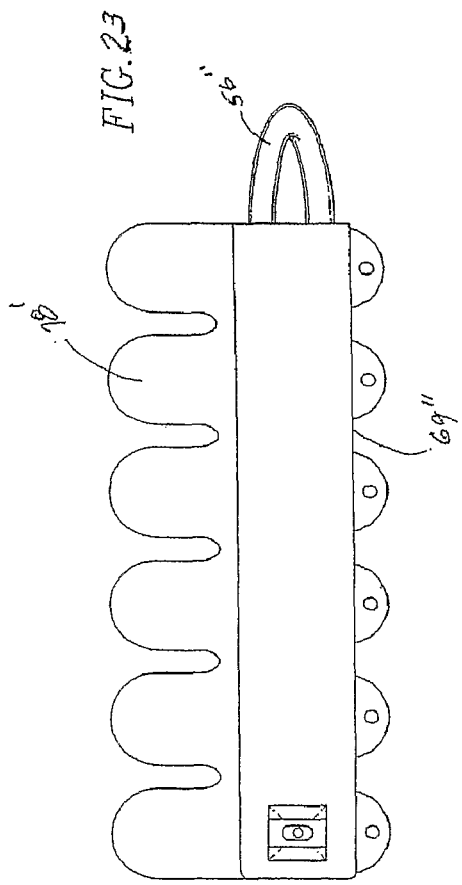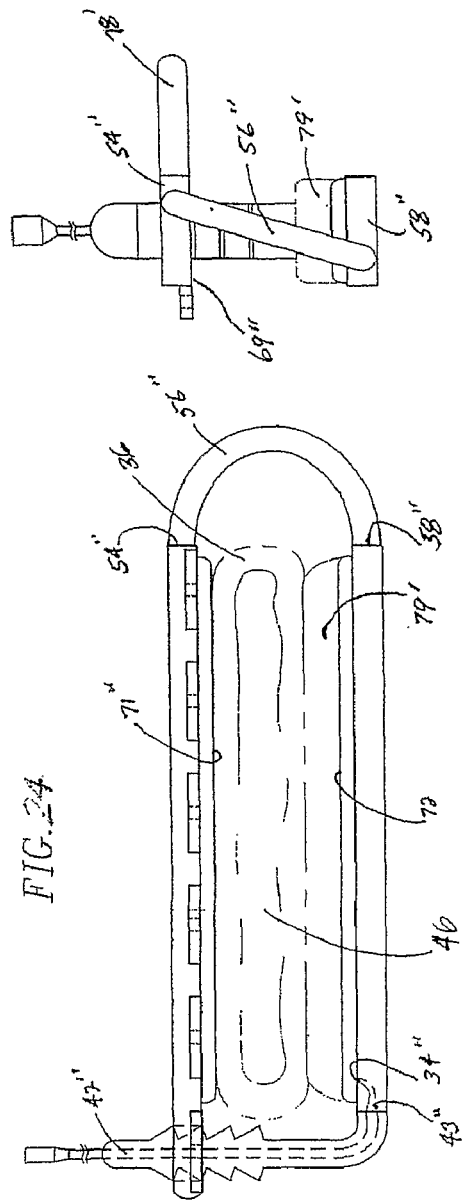

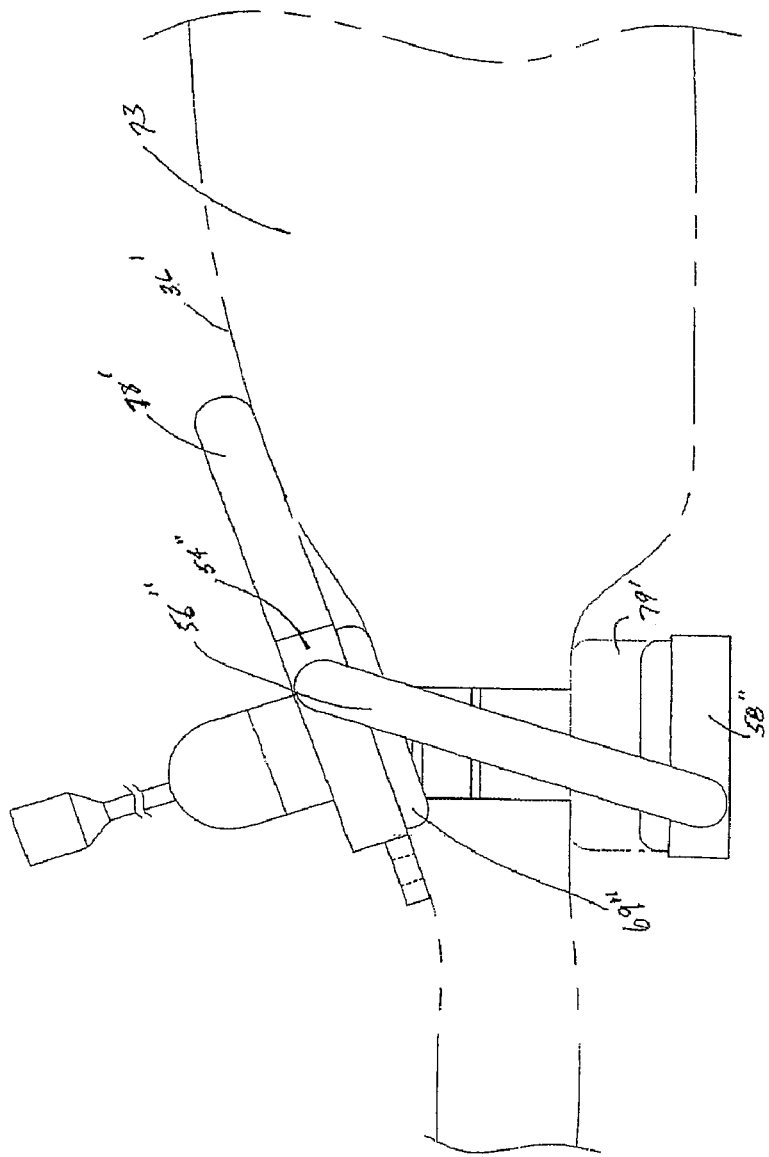

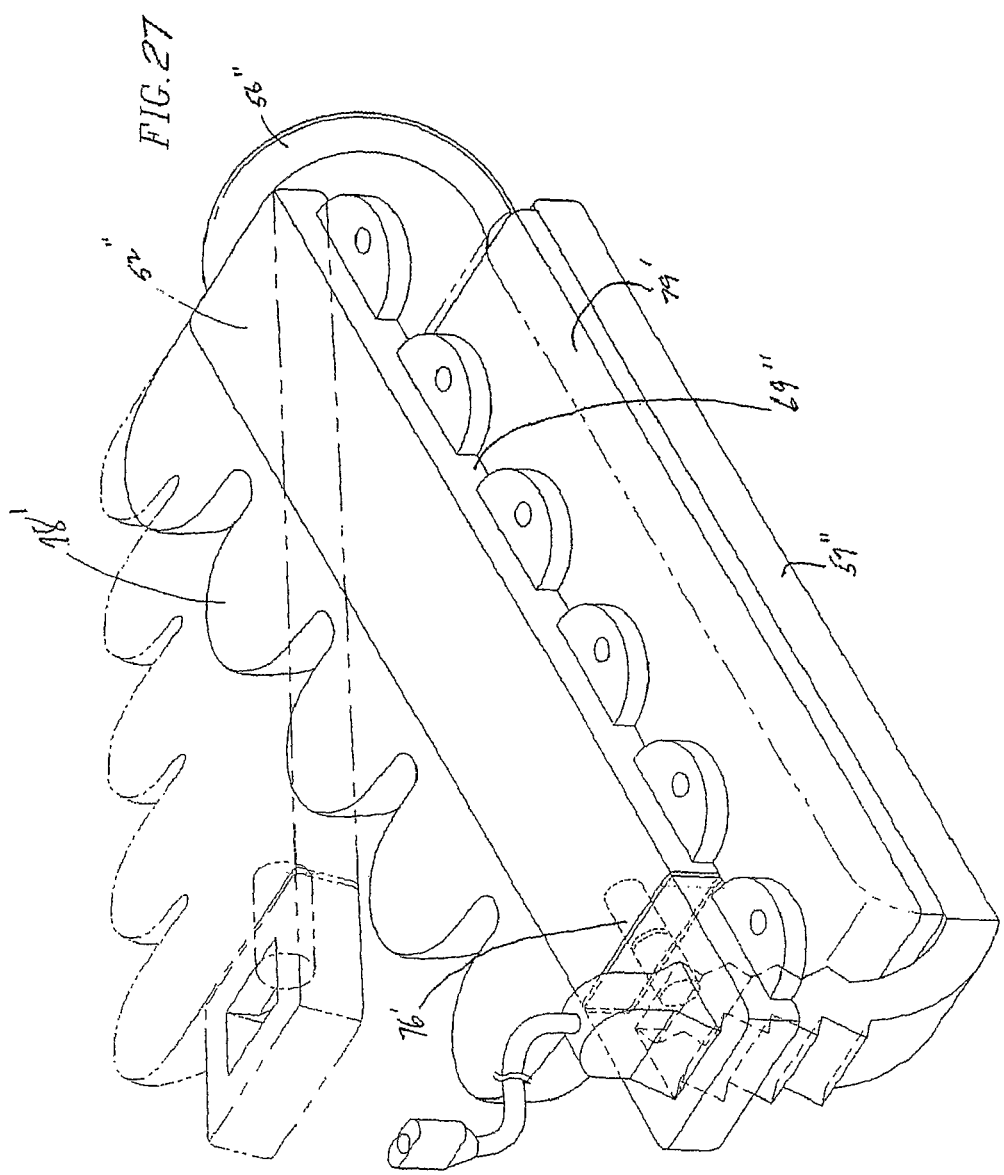

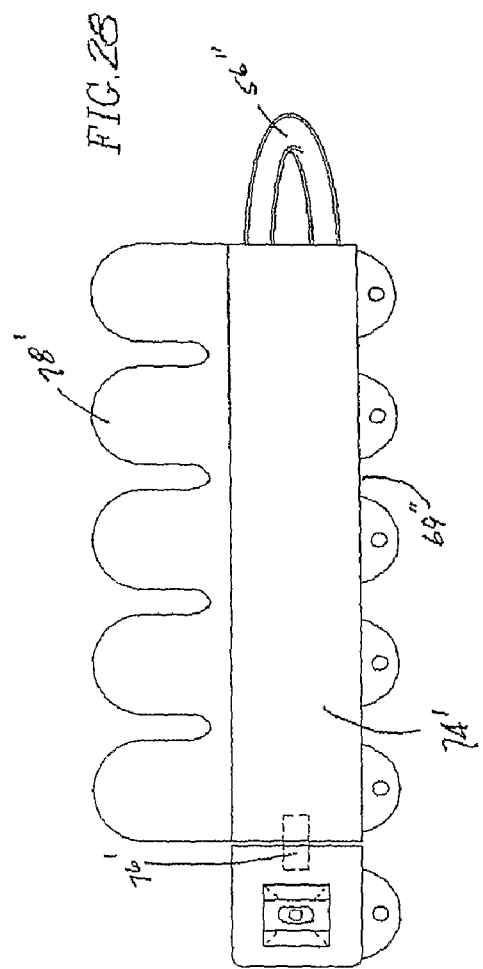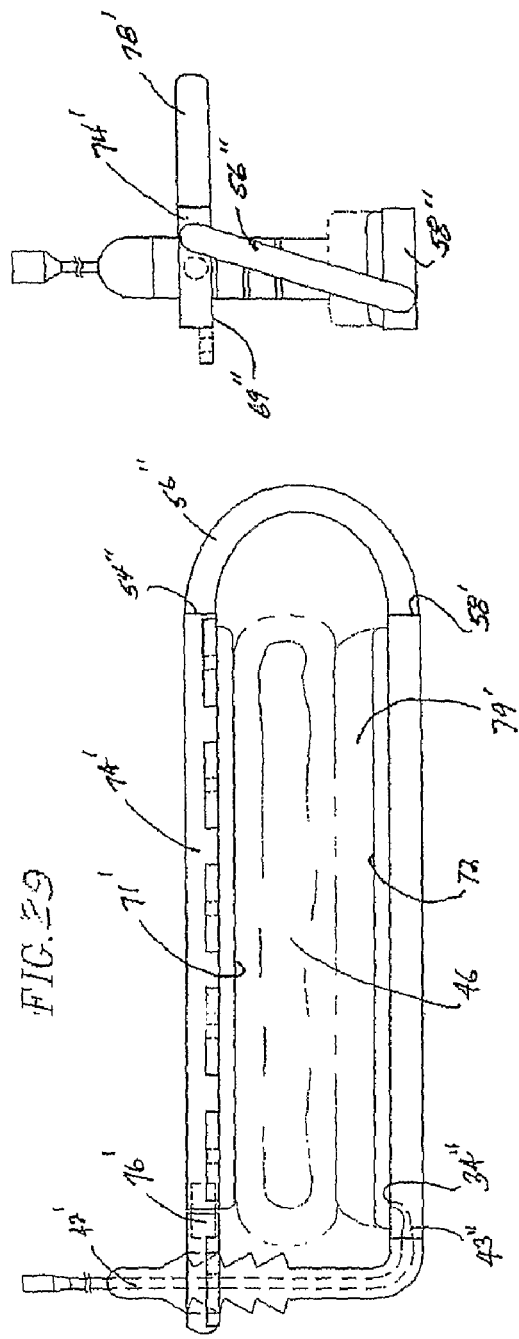

ated with a laterally extending bight portion where the bight portion has sufficient stiffness to retain the legs in fixed lateral spaced relationship at their hinged ends. The bight portion

CLAMP DEVICE TO PLICATE THE STOMACH

FIELD OF THE INVENTION

This invention relates to a medical device for clamping the stomach in morbid obesity bariatric surgery and for self-adjusting the resulting stoma of the gastric restriction.

BACKGROUND OF THE INVENTION

One of the most common illnesses is obesity. Many diseases are caused by or exacerbated by obesity, particularly in the western world, and these illnesses may be accompanied by physical and psychological disabilities. Surgical methods for controlling weight initially involved gastric stapling in various forms, which, over a prolonged period, resulted in major weight reduction. Because of the invasiveness of this type of surgery, and the irreversibility of it, the gastric stapling surgical technique was not widely accepted. These surgical procedures required a laparotomy which carried the risk of morbidity and death. Additionally, the gastric stapling technique required that the setting of the gastric restriction be initially set correctly because of the inability of the surgeon to modify the degree of restriction after the operation was performed. To overcome this difficulty, adjustable gastric banding was introduced which utilized an inflatable balloon carried by a band that could be placed around the stomach by an open operation or laparoscopically. The later technique has become the preferred surgical technique because of the reduced invasiveness of the operation. The degree of gastric restriction after placement of the band around the stomach immediately below the gastroesophageal junction was controlled by inflating an encircling balloon which was sealingly carried on the inner surface of the band; however, the bands of the prior art created the gastric restriction by annularly or hoop compressing the stomach. A possible consequence of annular stress is the inducement of erosion that permitted the band to go into the bowel thereby causing bleeding, infection, and even death.

Thus, it is desirable to provide a stomach plication device that avoids annular stress, that utilizes inflatable members to prolong the life of the plication device, that is laparoscopically implantable, avoids erosion, and is adjustable to control the gastric restriction stoma after the operation is completed. It would also be desirable to provide such a device that reduces and enlarges the stoma upon distention or contraction of the proximal stomach where the device is self-adjusting in response to distention and contraction.

SUMMARY OF THE INVENTION

There is, therefore, provided according to the present invention a fluid inflatable clamp device to plicate the stomach for morbid obesity surgery and substantially reduce the risk of band erosion resulting form annular compression of the stomach. The inflatable device is adjustable and can be placed laparoscopically or by open operation.

The present invention is directed to embodiments that utilize opposing legs carrying an inflatable balloon member to permit clamping of the stomach below the gastroesophageal junction. By selectively inflating or aspirating opposing balloons, the life of the clamp may be substantially prolonged and consequently the frequency of replacement surgery greatly reduced. The device is preferably made of silicone where the legs are so constructed and proportioned to have sufficient stiffness to permit limited bending and are so hinged such that the hinged ends of the legs are in fixed lateral spaced relationship.

In each of the embodiments of the invention, the fluid inflatable device to plicate the stomach is U-shaped and consists of a first leg or plate having a preferably rectangular shape where the first leg has a free first end and a hinged opposite end and an axis of elongation; a second leg having substantially the same configuration as the first leg also has a hinged end and free second end. The hinged ends of the legs are integrally connected to a laterally extending bight portion which has sufficient stiffness to retain the legs in fixed lateral spaced relationship at their hinged ends.

In the preferred embodiment, the first leg has a first lumen extending at least in part axially therein that communicates with a first inflation port and, likewise, the second leg has a second lumen extending at least in part axially therein that communicates with a second inflation port. However the second leg also has a third lumen extending axially therein that communicates with a bight lumen extending laterally through the bight portion where the bight lumen is in fluid communication with the first lumen. Thus, a flow path is provided that permits fluid flow for inflating or aspirating a first inflatable member that is peripherally sealed and extends axially along the inner surface of the first leg. A separate flow path is provided to permit fluid flow through the second lumen and second inflation port for inflating and aspirating a second inflatable member that is peripherally sealed and extends axially along the inner surface of the second leg; the second inflatable member is oppositely positioned from the first inflatable member when the stomach is clamped.

The embodiment above described further includes latch means associated with the first and second legs at their free ends to permit the legs to be locked in pre-determined fixed lateral relationship during the clamping of the stomach. Separate fluid flow paths are defined by first and second conduits which are contained within a flexible latch member having at least one serration where the flexible latch member is integrally carried by the second leg member adjacent its free end; the first conduit of the flexible latch member communicates with the second lumen and the second conduit of the flexible latch member communicates with the third lumen. Fluid supply means associated with the latch means permits saline fluid to be selectively supplied or aspirated through the first conduit to inflate or aspirate the first inflatable member to a pre-determined pressure. The second inflatable member may be separately inflated to a pre-determined pressure by the fluid supply means supplying or aspirating fluid through the second conduit of the flexible latch member. To secure the free ends of the first and second legs in substantially fixed lateral spaced relationship, the first leg has a latch cavity adjacent the free end so dimensioned and proportioned to permit locking engagement with a selected serration of the serrated flexible latch member.

In another embodiment of this invention, the inflatable device has, as in the preferred embodiment, a first leg, preferably of plate shape, an axis of elongation, a first end and a hinged end, a first inflation port, and a first lumen extending at least in part axially therein; a second leg having substantially the same rectangular plate configuration as the first leg, an axis of elongation, a hinged end, a free end, and a second lumen extending at least in part axially therein where the second lumen communicates with a second inflation port. The hinged ends of the legs are self hinged and integrally associcontains a laterally extending bight lumen that communicates with the first and second lumens thereby providing a fluid flow path to the first inflation port. The first inflatable member which is sealingly carried by the first leg extends at least in part axially on the inner surface of the first leg where the first inflatable member communicates with the first inflatable port. The second leg sealingly carries a second inflatable member which is oppositely positioned from the first inflatable member when the stomach is clamped between the first and second legs. As in the preferred embodiment above described, in this embodiment the serrated flexible latch member is carried by the second leg adjacent its free end and the flexible latch member contains a first conduit therein in fluid communication with the second lumen. To secure the free ends of the first and second legs in fixed space relationship, the first leg has a latch cavity adjacent to the free end that is so dimensioned and proportioned to permit locking engagement with a selected serration of the serrated flexible latch member. A fluid supply and aspiration means is associated with the serrated flexible latch member and communicates with the first conduit to selectively permit inflation or aspiration of both the first and second inflatable members.

In yet still another embodiment, the plication device is of similar construction as in the previous embodiments. As in the above described embodiments, the plication device is preferably U-shaped and has a first leg and a second leg which are preferably of a rectangular plate shape and self-hinged to the bight portion so as to permit the legs to articulate with respect to the bight portion. An axis of elongation extends through the first leg, bight portion, and second leg and a single inflatable member is sealingly carried and extends axially and continuously on the inner surface of the first and second legs and bight portion. The first leg has a first lumen that communicates with an inflation port that is in fluid communication with the single inflatable member. As in the above described embodiments, a flexible latch member is associated with the first and second legs for spacing the legs in substantially fixed spatial relationship where the flexible latch member contains at least one serration. The flexible latch member has a first conduit therein that is in fluid communication with the first lumen. A fluid supply means, as described in the above embodiments, is associated with the flexible latch member for selectively supplying and aspirating fluid through the first conduit to inflate or aspirate the inflatable member to a pre-determined pressure or lateral distance from the inner surfaces of the first and second legs.

The present invention is also directed to a self-adjusting clamp device that is U-shaped and self-adjusts the gastric restriction stoma of the plicated stomach. The plication device is clamped to the stomach distally of the gastroesophageal junction forming a proximal stomach portion intermediate the stoma and the junction. The stomach has an anterior surface and a posterior surface which are clamped by the inner surface of the first and second legs respectively as described in the above embodiments. The first and second legs have a free-end and a hinged-end where the hinged ends are interconnected with a bight portion and the free-ends by a latch that locks the free-ends in fixed spaced relationship. A lever carried by the first leg extends from the first leg in a direction toward the gastroesophageal junction and is in continuous compressive engagement with at least a part of the anterior surface of the proximal stomach. The lever pivots in response to distention and contraction of the proximal stomach. In one embodiment, the lever consists of a multiplicity of fingers forming a platform extending laterally from the first leg in a direction toward the gastroesophageal junction and compressively bear against the proximal stomach. The fingers are biased by a pair of resilient torsion members so carried by the platform and the first leg such that distention of the proximal stomach with food will cause the platform to rotate resulting in a reduction of the gastric restriction stoma; subsequent contraction of the proximal stomach towards the nominal gastric restriction stoma results in enlarging the stoma toward the nominal position.

In another embodiment, the bight portion is so constructed such that the bight portion is sufficiently rigid to maintain the lateral distance between the inner surfaces of the first and second legs in fixed spatial relationship at their hinged ends and sufficiently resilient, torsionally, to permit the platform to remain in compressive bearing relationship with the anterior surface of the proximal stomach. As in the previous embodiment, distention of the proximal stomach with food causes rotation of the platform resulting in a reduction of the gastric restriction stoma; and subsequent contraction of the proximal stomach results in enlarging the stoma towards its nominal position. In each of the embodiments above described, the first leg carries a multiplicity of eyelets for suturing the device to the stomach with permanent suture.

In yet another embodiment of the self-adjusting device of this invention, the finger platform is biased by a resilient torsion member interconnecting the first leg adjacent its free-end with the finger platform; and at the hinged end of the first leg, the bight portion is so constructed and proportioned such that it is sufficiently rigid to maintain the lateral distance between the inner surfaces of the first and second legs in fixed spatial relationship and is sufficiently resilient, torsionally, to permit the platform to remain in compressive bearing engagement with the anterior surface of the proximal stomach.

The embodiments above described for a self-adjusting clamp may include an inflatable member sealingly carried on the inner surface of the second leg for inflating the inflatable member or aspirating it to a pre-determined pressure after the device is positioned and clamped to the stomach.

BRIEF DESCRIPTION OF THE DRAWINGS

These and other features and advantages will become appreciated as the same become better understood with reference to the following specification, claims and drawings wherein:

FIG. 3 is a side view of FIG. 1 illustrating the preferred embodiment of this invention in a latched configuration with the stomach plicated.

FIG. 4 is a front view of FIG. 3.

FIG. 5 is a rear view of FIG. 3.

FIG. 6 is a top view of FIG. 3.

FIG. 8 is a side view of another embodiment of this invention.

FIG. 9 is a front view of FIG. 8.

FIG. 10 is a rear view of FIG. 8.

FIG. 11 is a top view of FIG. 8.

FIG. 12 is a perspective view of an embodiment of the self-adjusting stomach plication device of this invention illustrating the device in open and latched configurations.

FIG. 13 is a top view of the embodiment shown in FIG. 12.

FIG. 14 is a front view of the embodiment shown in FIG. 12 illustrating the nominal gastric restriction stoma after the stomach is plicated.

FIG. 15 is a right side view of FIG. 14.

FIG. 16 is a right side view of FIG. 14 illustrating the proximal stomach in phantom lines distended and pivoting the lever platform to reduce the gastric restriction stoma.

FIG. 17 is a perspective view of another embodiment of a self-adjusting stomach plication device having an inflatable member.

FIG. 18 is a top view of the embodiment shown in FIG. 17.

FIG. 19 is a front view of the embodiment shown in FIG. 17 illustrating both the plication of the stomach with an inflatable member inflated and the resulting nominal gastric restriction stoma.

FIG. 20 is a right side view of FIG. 19

FIG. 21 is a right side view of FIG. 19 illustrating the proximal stomach in phantom lines distended and pivoting the lever platform to reduce the gastric restriction stoma.

FIG. 22 is a perspective view of yet another embodiment the self-adjusting stomach plication device having an inflatable member.

FIG. 23 is a top view of the embodiment shown in FIG. 22.

FIG. 24 is a front view of the embodiment shown in FIG. 23 illustrating both the plication of the stomach with an inflatable member inflated and the resulting nominal gastric restriction stoma.

FIG. 25 is a right side view of FIG. 24.

FIG. 26 is a right side view of FIG. 24 illustrating the proximal stomach in phantom lines distended and pivoting the lever platform to reduce the gastric restriction stoma.

FIG. 27 is a perspective view of another embodiment of this invention having an inflatable member.

FIG. 28 is a top view of the embodiment shown in FIG. 27.

FIG. 29 is a front view of the embodiment shown in FIG. 27 illustrating the device in a latched position with the inflatable member inflated and the resulting nominal gastric restriction stoma.

FIG. 30 is a right-side view of FIG. 29.

DETAILED DESCRIPTION

Figure 1:
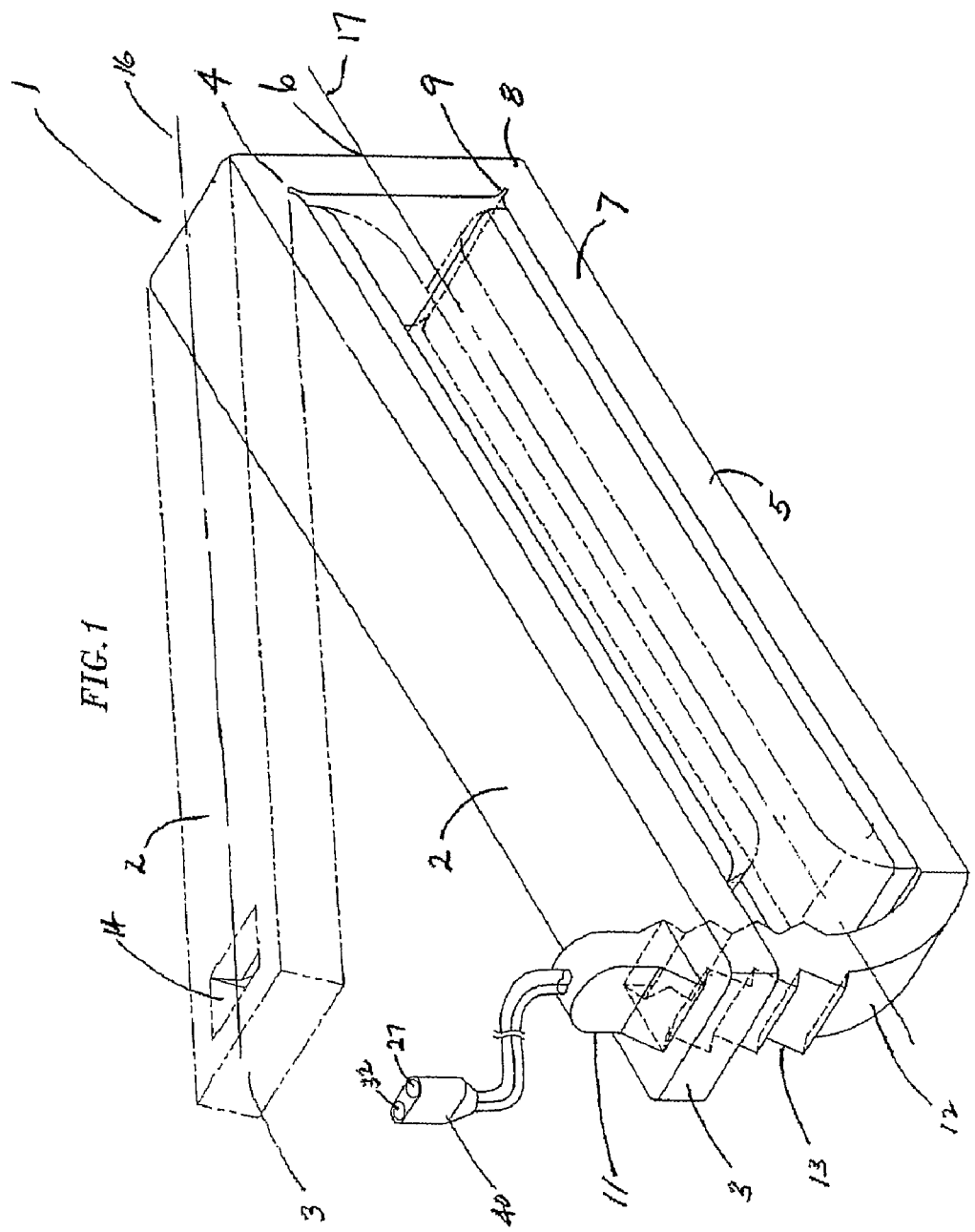
FIG. 1 is a perspective view of the preferred embodiment of the stomach plicating device of this invention for morbid obesity surgery illustrating the device in open and latched configurations.

FIG. 1 is a perspective of the preferred embodiment illustrating the stomach plication device 1 of this invention in both latched and unlatched configurations. As can be seen in FIG. 1, the first leg 2 is shown in phantom to depict the unlatched configuration; and the latched, closed configuration, is shown in solid lines. In the preferred embodiment the frame 5 of plication device 1 is U-shaped having a pair of opposing legs or rectangular plates interconnected by a bight and made of a silicone material. The frame consists of first leg or rectangular plate 2 which has a free-end 3 and a hinged-end 4. Hinged-end 4 is integrally connected and self-hinged to bight portion 6. First leg 2 is so constructed and proportioned to have sufficient stiffness to permit limited bending and to have sufficient flexibility at the juncture of the first leg and bight portion to rotate with respect to bight portion 6 at its hinged end 4. Bight portion 6 is also shaped rectangularly and is preferably made of a stiff silicone material with sufficient flexibility at the juncture of second leg 7 and bight portion 6 so as to form self-hinging joint 8; bight portion 6 is of sufficient stiffness such that the lateral distance between the hinged end 4 of first leg 2 and hinged end 9 of second leg 7 is essentially constant.

Figure 2:
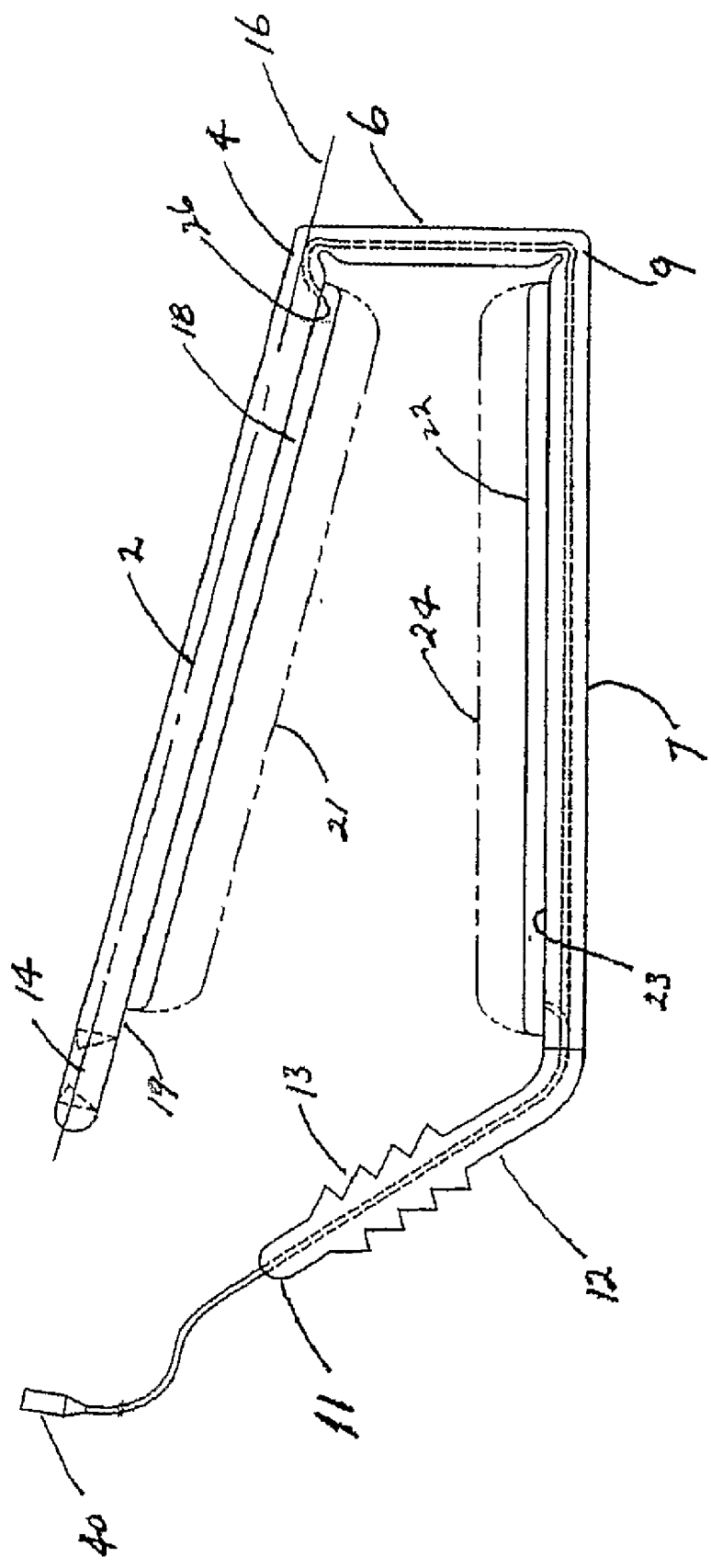
FIG. 2 is a side view of FIG. 1 illustrating the preferred embodiment in the unlatched open configuration.

Referring to FIGS. 1 and 2, it can be seen that second leg 7 has a free-end portion 11 that contains flexible latch member 12 which is bendable with respect to second leg 7 and consists of a multiplicity of serrations 13 to permit the forming of an adjustable latch lock with first leg 2. To form the latch lock, the serrations 13 are sequentially advanced through latch cavity 14 until a desired lateral separation between first leg 2 and second leg 7 is achieved. Each of the serrations 13 and latch cavity 14 are so dimensioned and constructed such that when a serration sufficiently engages latch cavity 14, the serration cannot be withdrawn back through the latch cavity.

Referring again to FIGS. 1 and 2, it can be seen that, first leg 2 has an axis of elongation 16 and second leg 7 has an axis of elongation 17. First inflatable member 18 is carried by first leg 2 and extends axially along inner surface 19 of the first leg. First inflatable member 18 is peripherally sealed to inner surface 19 and is selectively inflatable, preferably with saline fluid, to a desired lateral distance from inner surface 19 such as that illustrated in FIG. 2 by phantom line 21. In a like manner, second inflatable member 22 is peripherally sealed to inner surface 23 and extends axially along inner surface 23 of second leg 7 and is selectively inflatable with a saline fluid to a desired lateral dimension as illustrated in FIG. 2 by phantom line 24. In the preferred embodiment, first and second inflatable members are separately inflatable as hereafter described by reference to FIGS. 3, 4, 5, and 6.

As can be seen is FIG. 3, the stomach 36 is plicated between first leg 2 and second leg 7 by inflation of second inflatable member 22. First inflatable member 18 as shown in FIG. 3 has not been inflated while second inflatable member 22 is inflated to illustrate that either inflatable member or both can be used to further plicate the stomach 36 between the first and second legs.

The flow paths for inflating and aspirating inflatable members 18 and 22, and the corresponding inflation ports, can be seen by reference to FIG. 3. First leg 2 has a first inflation port 26 that communicates with first inflation member 18. Saline fluid for inflating first inflation member 18 is supplied from reservoir 40 through first conduit 27 that extends axially within flexible latch member 12 and communicates with third lumen 28. A fluid flow path is provided to first inflation port 26 by third lumen 28 which extends axially within and through second leg 7 and communicates with bight lumen 29. Bight lumen 29 extends laterally through bight portion 6 and in turn communicates with first lumen 31; first lumen 31 extends in part axially within first leg 2 completing the flow path to first inflation port 26. To inflate second inflatable member 22, a separate flow path is provided through second conduit 32 which extends axially through flexible latch member 12 and communicates with second lumen 33; second lumen 33 extends at least in part axially within second leg 7 and communicates with second inflation port 34. Thus, saline fluid may be separately supplied to inflate or aspirate second inflatable member 22 to a desired lateral dimension.

Figure 7:
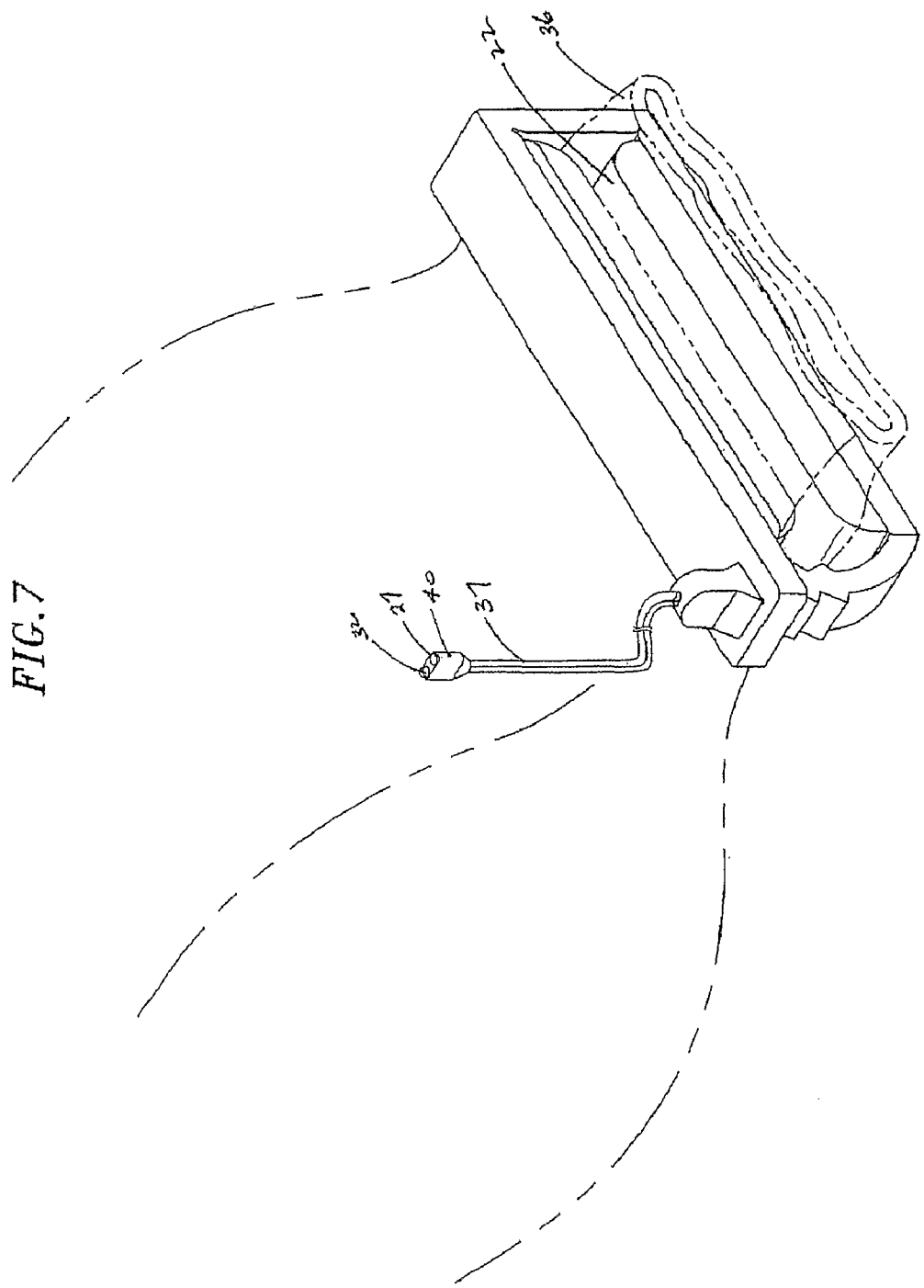
FIG. 7 is a perspective view of the preferred embodiment illustrating the device in latched configuration with the stomach plicated.
Figure 31:
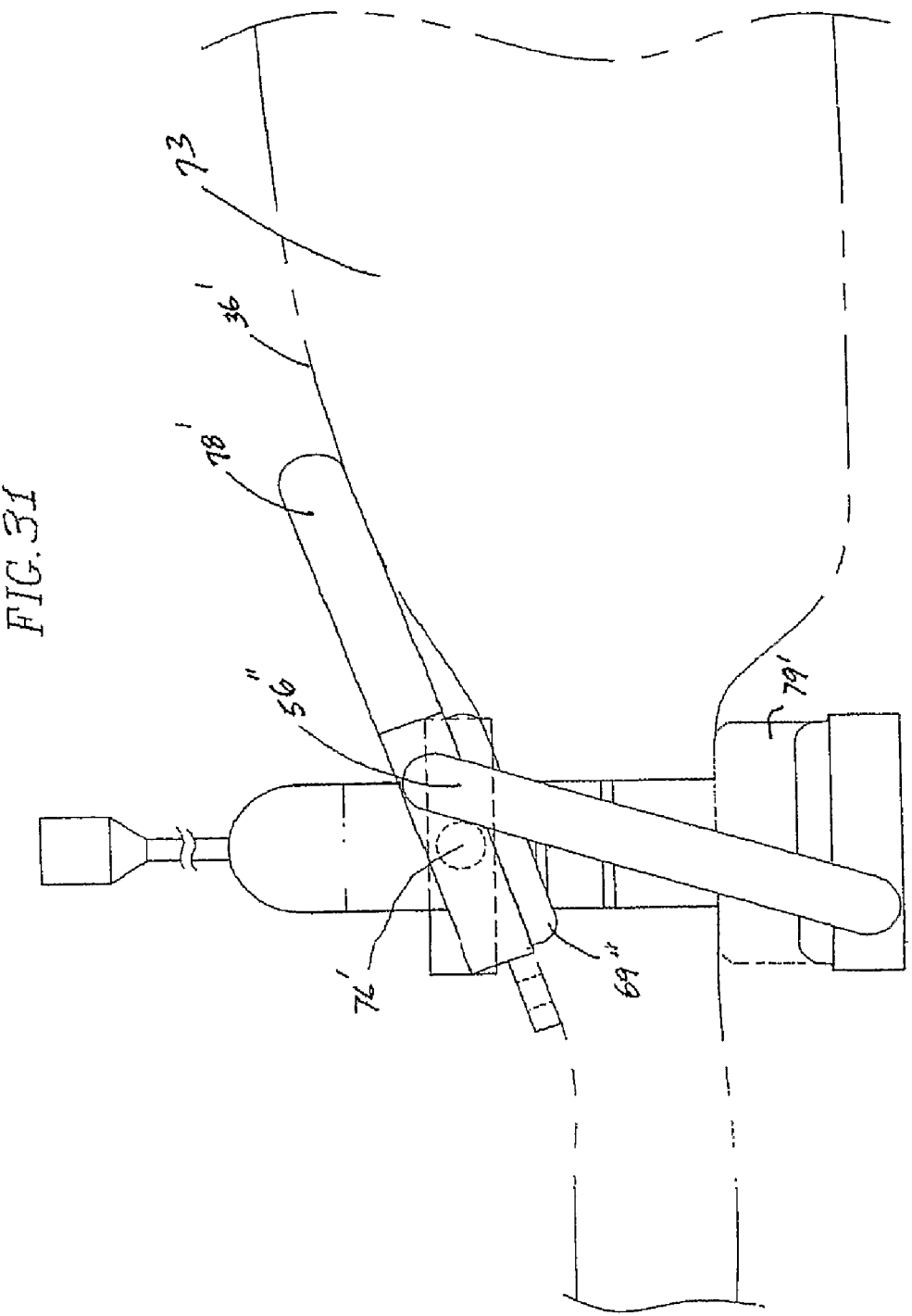
FIG. 31 is a right-side view of FIG. 29 illustrating the proximal stomach in phantom lines distended and the pivoting of the lever platform to reduce the gastric restriction stoma.

Referring now to FIG. 7, which is a perspective view of the preferred embodiment, stomach 36 is shown to be plicated between first leg 2 and second leg 7 with second inflatable member 22 sufficiently inflated to define a gastric restriction stoma. Although not shown in the drawings, a reservoir 40 is implanted in the patient and contains saline. Reservoir 40 communicates with conduits 27 and 32 which are contained within silicon tubing 37. Reservoir 40 is implanted during the operation within the left rectal muscle bed. The use of a silicone implanted reservoir to supply saline to inflate or aspirate a balloon is well known in the prior art and widely used in lap band gastric surgical procedures. The reservoir is attached to the anterior rectal sheath by absorbable sutures.

After the operation is completed, the gastric restriction stoma can be modified according to a patient's need. This is accomplished by use of a needle selectively inserted into injection ports carried by the reservoir. The reservoir has two injection ports located under the skin which can be localized radioscopically; the needle is then introduced into a respective port to inflate or aspirate the inflatable member communicating with that port. The preferred embodiment permits the surgeon after the plicating device has plicated the stomach to selectively inflate or aspirate either or both inflatable members to modify the gastric restriction stoma.

Another embodiment of this invention is illustrated in FIGS. 8, 9, 10, and 11. The basic distinction between this embodiment and the preferred embodiment described above is that a single inflatable member 38, shown in FIG. 8, is utilized rather than two separately inflatable members. By referring to FIG. 8, it can be seen that inflatable member 38 extends axially along the inner surface 19' of first leg 2', laterally along the inner surface 39 of bight portion 6', and axially along the inner surface 23' of second leg 7'. Single inflatable member 38 is peripherally sealed to the inner surfaces of first leg 2', bight portion 6', and second leg 7'; the expansion of single inflatable member 38 upon inflation is shown in FIG. 8 by phantom line 41. Inflation and aspiration of single inflatable member 38 is illustrated by reference to FIGS. 8, 9, and 11. As can be seen in FIG. 11, a single conduit 42 extends within and through flexible latch member 12' and as shown in FIG. 8 communicates with lumen 43 which extends at least in part axially within second leg 7' and communicates with inflation port 34'. Although not shown, a saline reservoir is implanted in the patient and communicates with conduit 42 to supply and aspirate saline to and from single inflatable member 38. As described above in the description of the preferred embodiment, the use of a silicone implanted reservoir 40 to supply saline to inflate or aspirate a balloon in lap band gastric surgery is well known. The reservoir is implanted during the operation within the left rectal muscle bed. After the operation is completed, the gastric restriction stoma can be modified by locating a reservoir injection port radioscopically and introducing a needle into the port to inflate or aspirate the inflatable member.

In yet another embodiment of this invention, not shown, the plication device is U-shaped and utilizes first and second inflatable members which are peripherally sealed and carried on the inner surface of the first and second legs, respectively as in the preferred embodiment; however, the device in this embodiment has a single fluid flow path to inflate the first and second inflatable members. The flow path consists of a conduit within the flexible latch member that communicates with reservoir 40, a first lumen that extends at least in part axially within the first leg, a bight lumen that extends laterally within the bight portion, and a second lumen extending axially within the second leg. The first and second inflatable members communicate with a respective inflation port and the inflation ports are in fluid communication with the first and second lumens. And as above described, the use of a silicone implanted reservoir 40 which is well known in the prior art permits inflation and aspiration of the first and second inflatable members. The gastric restriction stoma may be modified after the stomach is plicated and one of the flexible latch member serrations locked with respect to the first and second legs. As in the above described embodiments, reservoir 40 has an injection port that can be located radioscopically and accessed by a needle to supply or aspirate saline to inflate or aspirate the inflatable members.

FIG. 12 illustrates in perspective an embodiment of the self-adjusting clamp device of this invention that adjusts the gastric restriction stoma or opening in response to the distention and contraction of the proximal stomach after the stomach has been plicated. The proximal stomach is that portion of the stomach intermediate the gastroesophageal junction and the gastric restriction stoma. In FIG. 17, essentially the same structure for the self-adjusting clamp is shown; however, in FIG. 17, the structure includes an inflatable member for optionally adjusting the nominal stoma or opening of the stomach after it is clamped. Another embodiment is illustrated in FIG. 22 having an alternative structure to adjust the gastric restriction stoma in response to the distention or contraction of the proximal stomach; the embodiment shown in FIG. 22 includes an inflatable member which adjusts the nominal opening stoma after the stomach is clamped.

Another embodiment is shown in perspective in FIG. 27 illustrating yet another means for adjusting the gastric restriction stoma in response to distention and contraction of the proximal stomach. The device illustrated in FIG. 27 includes an inflatable member for optionally adjusting the nominal stoma after the stomach is clamped.

As can be seen by referring to FIG. 12, an embodiment of the self-adjusting clamping device 51 is shown which has a U-shaped frame 55 consisting of a first-leg 52 having a free-end 53, a hinged end 54, and a bight portion 56 interconnecting first leg 52 with second leg 57. FIG. 12 illustrates first leg 52, in phantom, articulating or pivoting with respect to its hinged end 54 which is integrally connected and self-hinged to bight portion 56. First leg 52 is also shown in solid lines latched to second leg 57. Bight portion 56 is of sufficient stiffness such that the lateral distance between self-hinged joint 58 and hinged end 54 remains essentially fixed.

As can further be seen in FIG. 12, second leg 57 has a free-end portion 61 that contains flexible latch member 62 which is flexible with respect to second leg 57 and contains a multiplicity of serrations 63 for forming a latch lock with first leg 52. As heretofore described, to form the latch lock, serrations 63 are sequentially advanced through latch cavity 64 until the desired lateral separation between first leg 52 and second leg 57 is achieved. As shown in FIG. 14, gastric restriction stoma 46 is formed by stomach 36 clamped between the first and second legs.

After the stomach 36 is clamped, self-adjust device 51 is sutured to the anterior stomach surface 36' with a permanent suture such as a silk suture or "Ethibond polydeck" ("Ethibond polydeck" is a registered trademark of Johnson & Johnson) through a multiplicity of eyelets 65 which extend through a plurality of eyelet tabs 66 that protrude laterally from distal edge 69 of first leg 52.

As shown in FIG. 12, first leg 52 has an axis of elongation 67 and second leg 57 has an axis of elongation 68 which, after the latch lock is formed, are essentially parallel. Inner surface 71 of first leg 52 and inner surface 72 of second leg 57 bear compressively against anterior surface 36' and posterior stomach surface 36", respectively, after the latch is formed.

Proximal stomach 73 is that portion of stomach 36 that extends proximally from self-adjusting clamp 51 to the gastroesophageal junction (not shown). When food enters into the stomach, proximal stomach 73 will distend as shown in FIG. 16. Self-adjusting clamp 51 in response to this distention will reduce the nominal gastric restriction stoma 46 (also shown in FIG. 16 by arrow A) to the stoma illustrated in FIG. 16 by arrow B thereby limiting even further the passage of food through the stoma. By referring to FIGS. 12, 13, and 14 it can be seen that first leg 52 is comprised of a platform member 74 that is pivotally connected to free-end 53 by resilient torsion member 76 and to hinged end 54 by resilient torsion member 77. Platform member 74 has a multiplicity of finger members 78 integrally carried by platform member 74 that extend laterally and proximately from first leg 52 in the direction of the gastroesophageal junction. Platform 74 and finger members 78 are made of a stiff silicone material and are so dimensioned, constructed, and adapted so as to bear compressively against anterior surface 36' and are biased to remain in continuous compressive engagement with anterior surface 36' by resilient torsion members 76 and 77. Platform 74 and finger members 78, although not shown in the figures, may be reinforced by a thin titanium plate over which silicone coating may be deposited. Although FIGS. 12, 13, 14, and 15 illustrate resilient torsion members 76 and 77 to be of a cylindrical shape, the torsion members may have a prism, square, or polygonal shape to permit the torsion member to be carried in fixed rotational relationship by platform 74 at the respective free and hinged ends of first leg 52.

Another embodiment of this invention is shown in FIGS. 17, 18, 19, 20, and 21. With the exception of inflatable member 79 that is sealingly carried on the inner surface 72 of second leg 57 and the fluid communication system to inflate or aspirate inflatable member 79, the structure of this embodiment is identical to that described above in FIGS. 12, 13, 14, 15, and 16 in relation to self-adjusting device 51. In FIG. 8, an inflation and aspiration system was shown and described by reference to a single conduit 42 that communicated with a reservoir 40, and extended through flexible latch member 12'. Conduit 42 also communicated with lumen 43 that extended at least part in part within second leg 7' where lumen 43 also communicated with inflation port 34'. Likewise, by referring to FIGS. 17, 18, and 19, it can be seen that single conduit 42' communicates with reservoir 40' for supplying or aspirating saline and extends through latch member 62 where single conduit 42' further communicates with lumen 43' and inflation port 34''. Although not shown in the Figures, reservoir 40 is implanted in the patient. Thus, the nominal stoma of gastric restriction stoma 46 may be reduced by inflating inflatable member 79. Thereafter, as shown in FIG. 21, finger members 78, which are biased to continuously bear compressively upon anterior stomach surface 36' by resilient torsion members 76 and 77, will reduce gastric restriction stoma 46 as food entering the stomach causes proximal stomach 73 to distend. Since finger members 78 are in continuous compressive bearing engagement with anterior surface 36', contraction of proximal stomach 73 will enlarge the stoma towards its nominal position.

FIGS. 22, 23, 24, and 26 illustrate yet another embodiment of the self-adjusting stomach plication device 51" of this invention. As in embodiment 51' shown and described in FIGS. 17, 18, 19, 20, and 21, embodiment 51" has an inflatable member 79', a first leg 52" which has a hinged-end 54", and a second leg 57" that has a hinged-end 58". Bight portion 56" is so constructed and adapted such that the lateral distance between inner surface 71" of first leg 52" and inner surface 72" of second leg 57" remains substantially constant after the first and second legs are latched together. Single conduit 42" (shown in FIG. 24) communicates with reservoir 40" for supplying or aspirating saline and extends through the latch member where conduit 42" further communicates with lumen 43" and inflation port 34". As in the previous embodiments described above for a self-adjusting stomach plication device, the first leg of embodiment 51" has a multiplicity of finger members 78' that extend laterally from the first leg in a direction toward the gastroesophageal junction. By referring to FIG. 25, it can be seen that bight portion 56" extends diagonally between the distal edge of second leg 57" and proximal edge of first leg 52"; bight portion 56" is so constructed and adapted so as to be torsionally resilient such that finger members 78' upon distention of the proximal stomach will remain biased in compressive engagement with anterior surface 36' of stomach 36 causing the distal edge 69" of first leg 52" to be rotationally displaced thereby reducing the gastric restriction stoma 46 from its nominal position. Upon contraction of the proximal stomach, the torsional resilence of bight portion 56" will bias finger members 78' to remain in compressive engagement with anterior stomach surface 36" and enlarge the gastric restriction stoma towards its nominal position.

Referring now to FIGS. 27, 28, 29, 30, and 31 it can be seen that in the embodiment illustrated by the Figures, that the difference between this embodiment and the embodiment of FIGS. 22, 23, 24, 25, and 26 is that free end 53" of first leg 52" is torsionally connected by resilient torsion member 76' to platform member 74' which has a hinged-end connected to torsionally resilient bight portion 56" as shown in FIGS. 22, 23, 24, 25, and 26.

While I have shown and described embodiments of a stomach plication device for morbid obesity surgery, it is to be understood that the invention is subject to many modifications without departing from the scope and spirit of the claims recited herein.

What is claimed is:

1. A self-adjusting clamp device to control weight loss by self-adjusting the gastric restriction stoma of a plicated stomach, said stomach having an anterior surface, a posterior surface, and a proximal stomach portion intermediate the gastroesophageal junction and said gastric restriction stoma, comprising:
   a. a frame comprising a first leg having an axis of elongation a first free end, a hinged end, and an axially extending inner surface;
   b. said frame further comprising a second leg in lateral spaced relationship with said first leg, said second leg having an axis of elongation, a second free end, a hinged end, and an axially extending inner surface, said frame further having a bight portion integrally connecting said hinged ends of said first and second legs so as to permit said first leg to articulate with respect to said second leg;
   c. latch means associated with said first and second legs for locking said first free end and said second free end in fixed lateral spaced relationship;
   d. lever means carried by said first leg responsive to distention and contraction of said proximal stomach portion for reducing and enlarging said gastric restriction stoma; and
   e. bias means associated with said lever means for biasing said lever means in continuous compressive engagement with at least a part of said anterior surface of said proximal stomach portion such that when said proximal stomach portion is distended by food said lever means in response to said distention will reduce said gastric restriction stoma and upon contraction of said proximal stomach portion will enlarge said reduced gastric restriction stoma.

2. The self-adjusting clamp device recited in claim 1 where said lever means comprises a platform member carried by said first leg and a multiplicity of finger members extending laterally from said platform member for compressive bearing engagement with said anterior surface of said proximal stomach portion.

3. The self-adjusting clamp device recited in claim 2 where said bias means comprises a resilient torsion member carried by said free end of said first leg and so adapted to said platform member to permit said platform member to rotate with respect to said free end.

4. The self-adjusting clamp device recited in claim 3 where said bias means comprises a resilient torsion member carried by said hinged end of said first leg and so adapted to said platform member to permit said platform member to rotate with respect to said hinged end.

5. The self-adjusting clamp device recited in claim 2 where said bias means comprises said bight portion where said bight portion is torsionally resilient and so constructed and adapted to said hinged ends of said first and second legs to bias said multiplicity of finger members in compressive bearing engagement with said proximal stomach portion.

6. The self adjusting clamp device recited in claim 3 where said bias means further comprises said bight portion where said bight portion is torsionally resilient and so constructed and adapted to said hinged ends of said first and second legs to bias said multiplicity of fingers in compressive bearing engagement with said proximal stomach portion.

\* \* \* \* \*